United States Patent [19]
Yuan et al.

[11] Patent Number: 5,387,212
[45] Date of Patent: Feb. 7, 1995

[54] VERTEBRAL LOCKING AND RETRIEVING SYSTEM WITH CENTRAL LOCKING ROD

[76] Inventors: Hansen A. Yuan, 5066 Pine Valley Dr., Fayetteville, N.Y. 13066; Chih-I Lin, 513 S. Golden Pardos Dr., Diamond Bar, Calif. 10765

[21] Appl. No.: 9,043
[22] Filed: Jan. 26, 1993
[51] Int. Cl.⁶ .................................. A61B 17/56
[52] U.S. Cl. .................................... 606/61
[58] Field of Search ............. 606/61, 53, 60, 59, 606/54, 72, 73

[56] References Cited

U.S. PATENT DOCUMENTS

| | | | |
|---|---|---|---|
| 5,176,680 | 1/1993 | Vignaud et al. | 606/60 |
| 5,254,118 | 10/1993 | Mirkovic | 606/60 |

FOREIGN PATENT DOCUMENTS

| | | | |
|---|---|---|---|
| 2499400 | 8/1982 | France | 606/59 |
| 556793 | 6/1977 | U.S.S.R. | 606/61 |
| 1544409 | 2/1990 | U.S.S.R. | 606/61 |

OTHER PUBLICATIONS

"Scoliosis & Spinal Instrumentation Systems" catalog of Zimmer Company, Warsaw, Indiana 46580.
"R. Roy-Camille Francobal's' Plates" catalog of Howmedica, Inc., U.S.A.
"Universal Instrumentation (CD) For Spinal Surgery" catalog of Sofamor Company, B.P. 139, 62604 Berck-Su Mer Cedex France.
"TSRH Spinal System" catalog of Danek Group, Inc., 3092 Directors Row, Memphis Tenn. 38131.
"Isola Spinal System" catalog of AcroMed Corporation, U.S.A.

Primary Examiner—Tamara L. Graysay
Attorney, Agent, or Firm—Bacon & Thomas

[57] ABSTRACT

A vertebral locking and retrieving system includes a plurality of horizontal locking and retrieving member sets, a plurality of vertebral locking members, a plurality of connecting member sets, and a central locking rod. Each of the horizontal locking and retrieving member sets is composed of a locking rod retainer and two locking member retainers fastened respectively to two opposite sides of the locking rod retainer. Each of the vertebral locking members has one end for locking a vertebra and another end fastened to one of the locking member retainers. The connecting member sets are used in fastening the vertebral locking members to the locking member retainers and in fastening the central locking rod to the locking rod retainer. A horizontal locking of a vertebra is achieved by the horizontal locking and retrieving member sets while a longitudinal locking of the vertebra is attained by the central locking rod connecting the horizontal locking and retrieving member sets.

11 Claims, 4 Drawing Sheets

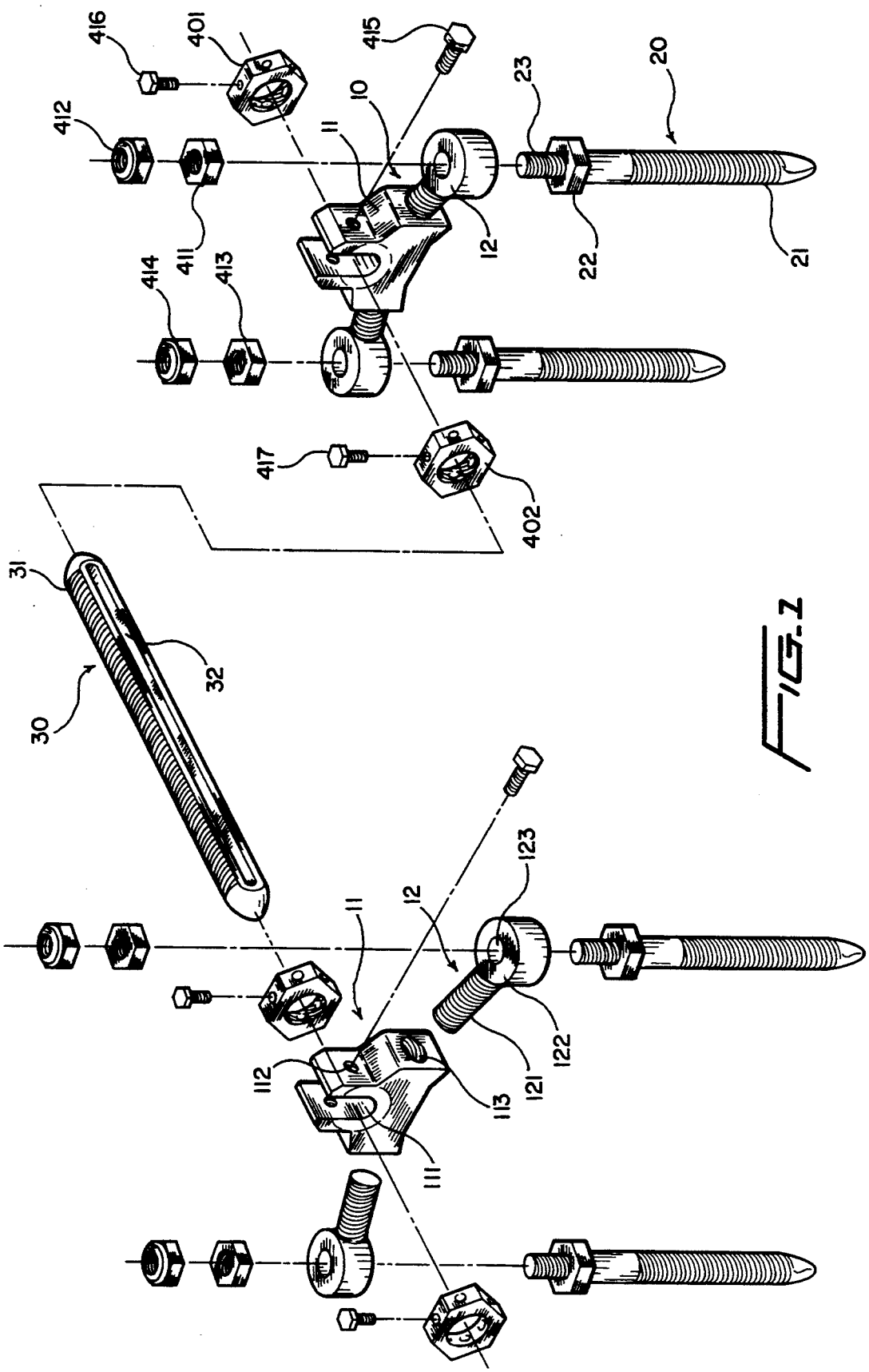

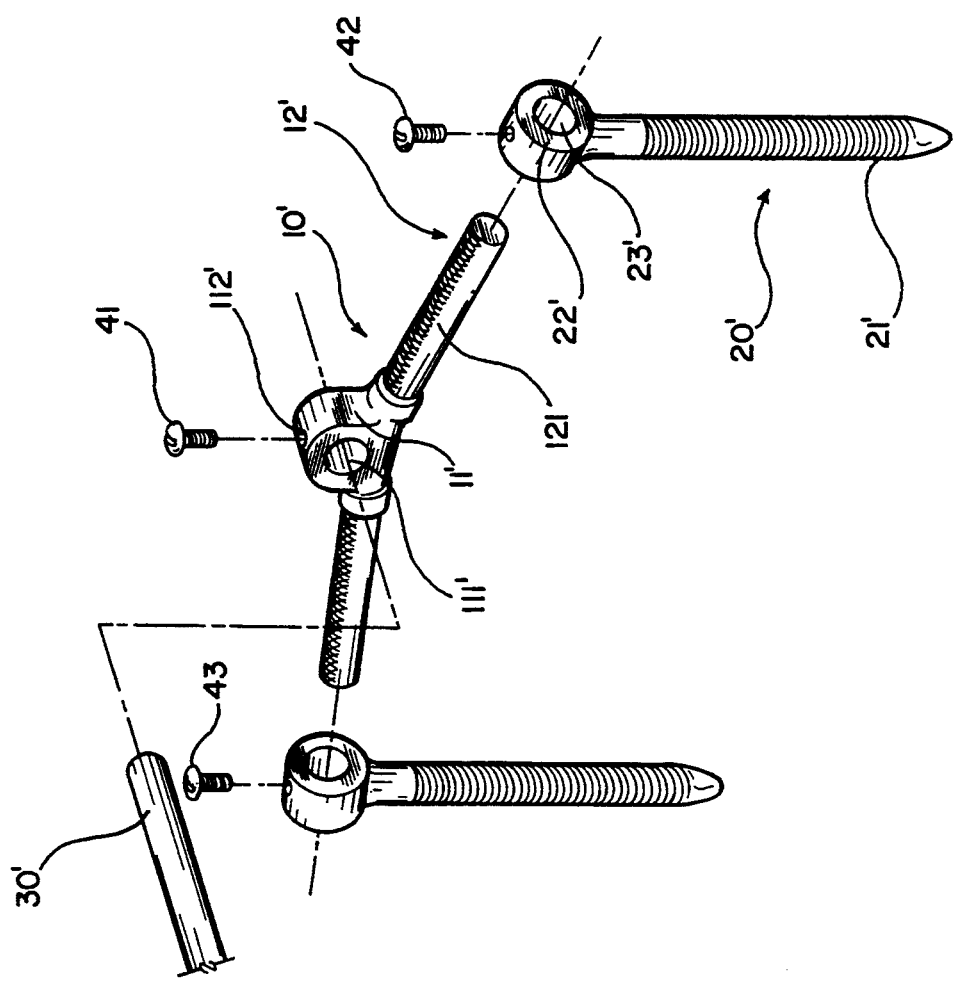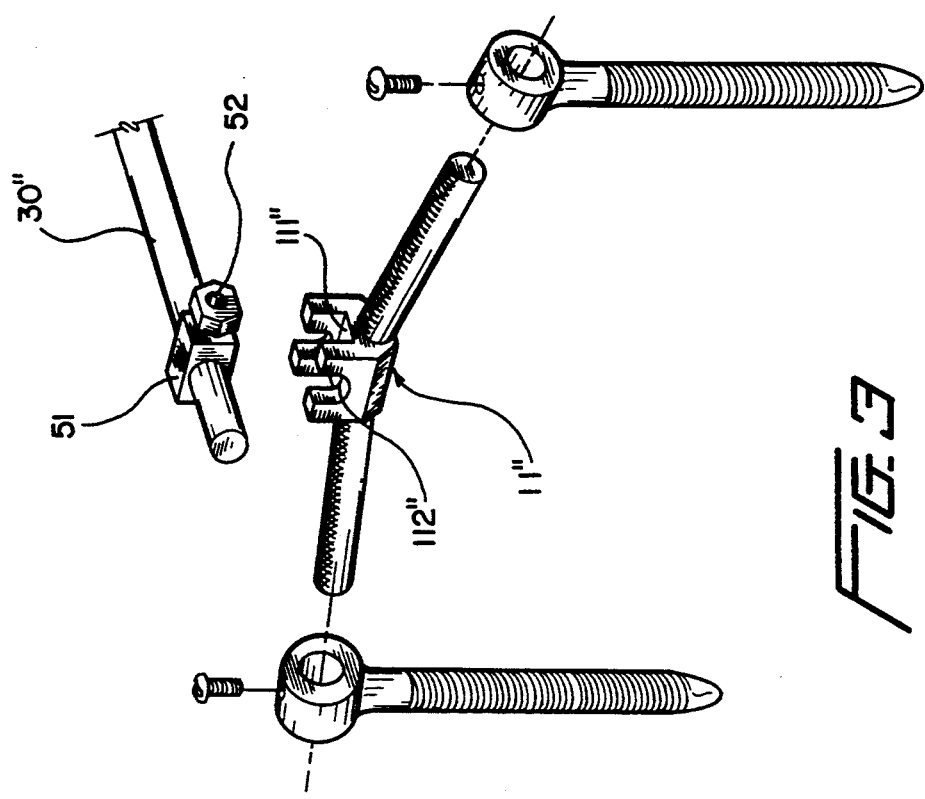

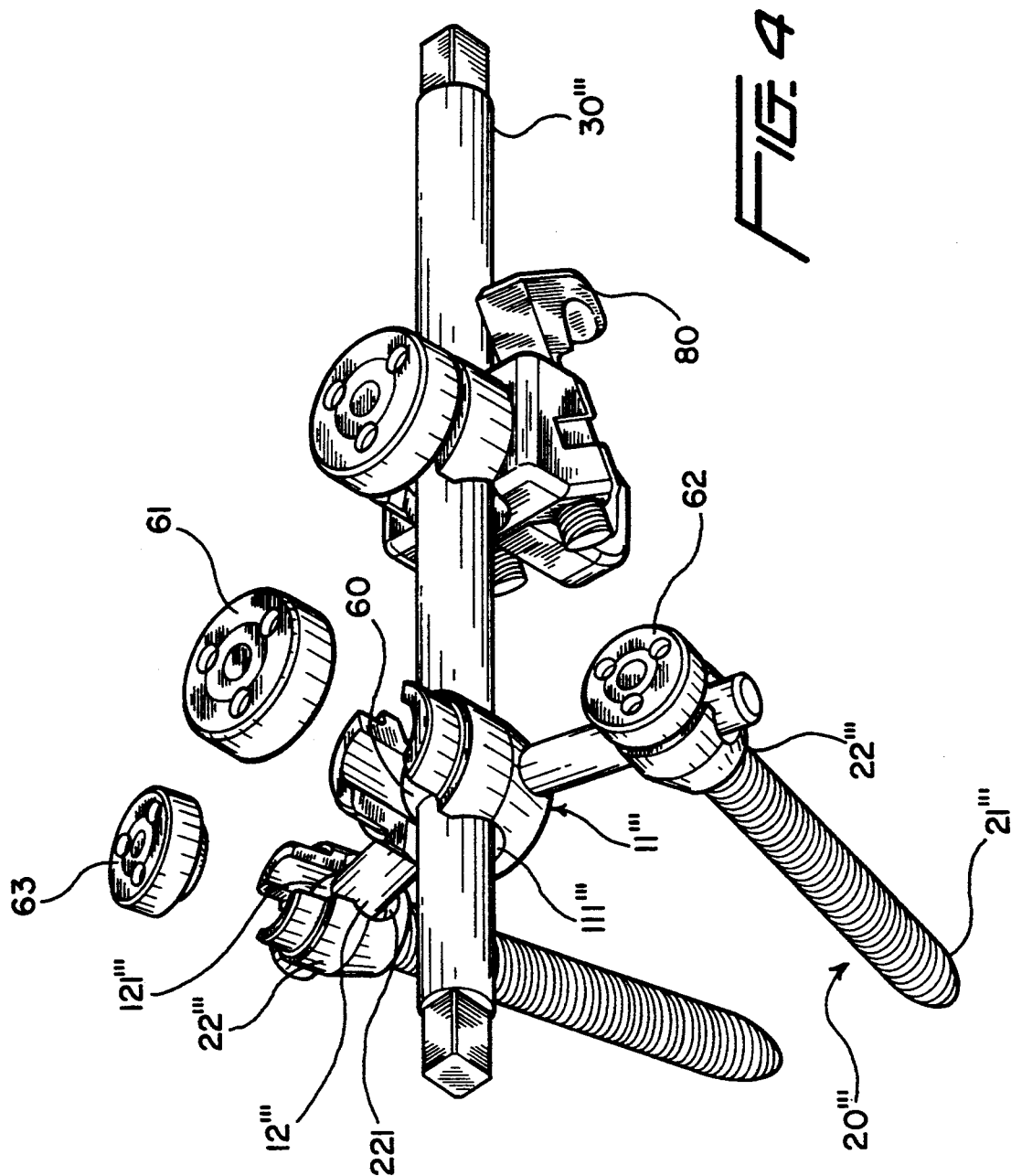

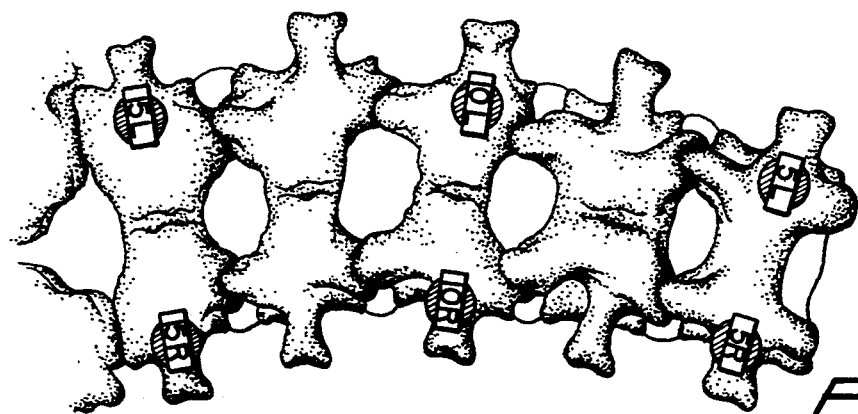
FIG. 5-a
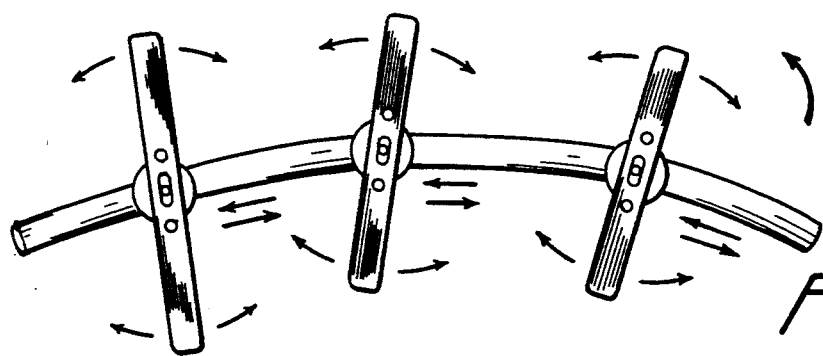
FIG. 5-b
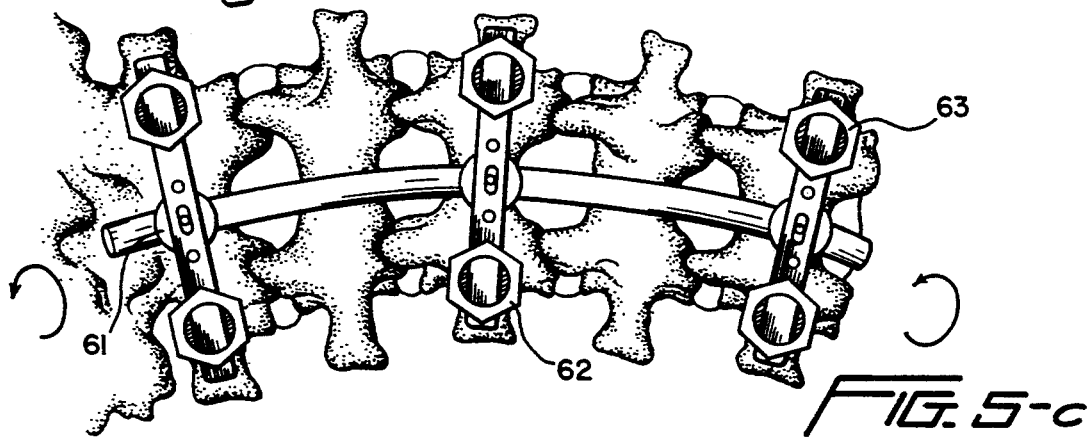
FIG. 5-c
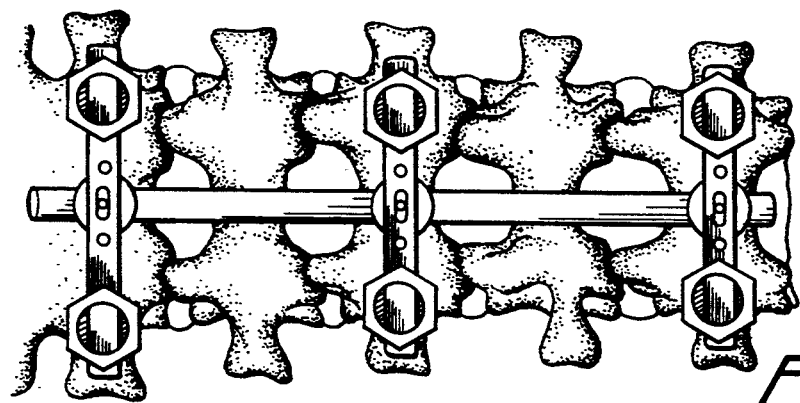
FIG. 5-d

VERTEBRAL LOCKING AND RETRIEVING SYSTEM WITH CENTRAL LOCKING ROD

FIELD OF THE INVENTION

The present invention relates to a vertebral locking and retrieving system, and more particularly to an improved vertebral locking and retrieving system with a central rod for use in the surgical treatment of scoliosis.

BACKGROUND OF THE INVENTION

In general, conventional vertebral locking and retrieving systems of the prior art involve a locking process of multiple vertebrae, as exemplified by rods sold under the trademarks LUGUE and HARRINGTON, both made by Zimmer Company of U.S.A., and plates sold under the trademark ROYCAMMILE produced by Howmedia Corporation of U.S.A. Such known prior art arrangements require a surgeon to make a long incision, which generally takes up too much of a surgeon's time and may bring about an excessive bleeding by a patient receiving the treatment. The case in point is the LUGUE rod, which must be secured to two upper and lower vertebrae immediately adjacent to the injured or the deformed vertebra. This means that a surgeon is required to make a large incision to fix at least five segments of the spinal column. As a result, the patient's ability to move about is greatly hampered in the wake of such a surgical operation. In addition, the pressure exerting on the patient's nervous system by the locking and retrieving system of the prior art can not be effectively mitigated in view of the facts that the locking process is confined to a rear plate and that the retrieval of a front plate is not possible.

The prior art device for use in correcting the lateral curvature of the spine, such as the CD scoliosis correcting device made by Sofamor Company of France, is defective in design in that its lateral correcting effect is so limited as to result in an unequal intervertebral distance on both sides of the vertebrae. In addition,, the prior art device mentioned above has a serious drawback that it is unable to provide a simple and effective locking mechanism either in the longitudinal direction or in the horizontal direction.

With a view to overcoming the drawbacks of the above-mentioned systems and approaches of the prior art, one of the present inventors, Chih-I Lin, discloses an improved vertebral locking and retrieving system in U.S. Pat. No. 5,176,679. However, such a system is not suitable for use in the surgical treatment of scoliosis, especially osteoporotic degenerative scoliosis.

SUMMARY OF THE INVENTION

It is, therefore, the primary objective of the present invention to provide a vertebral locking and retrieving system with a central rod, which can be used in a surgical operation for locking and retrieving a deformed vertebra as well as in a surgical operation for correcting the scoliosis.

It is another objective of the present invention to provide a vertebral locking and retrieving system with a central rod, by which the horizontal locking mechanism can be brought about prior to the longitudinal locking mechanism.

It is still another objective of the present invention to provide a vertebral locking and retrieving system with a central rod, by which two or more segments of the spinal column can be locked in place.

It is still another objective of the present invention to provide a vertebral locking and retrieving system with a central rod, which has a superb quality of being capable of locking and retrieving the vertebrae, without being susceptible to an interference by a torsion or a shearing force.

It is still another objective of the present invention to provide a vertebral locking and retrieving system with a central rod, which is suitable for use in the surgical treatment of scoliosis.

It is still another objective of the present invention to provide a vertebral locking and retrieving system with a central rod, which is in fact composed of a plurality of horizontal locking and retrieving members, vertebral locking members, and connecting members, in addition to a central rod.

In keeping with the principles of the present invention, the foregoing objectives of the present invention are attained by a vertebral locking and retrieving system with a central rod. The system comprises a plurality of horizontal locking and retrieving members, vertebral locking members, and connecting members, in addition to a central locking rod.

The system of the present invention is characterized in that it facilitates a horizontal locking of a vertebra as well as a longitudinal locking of the vertebra by means of the horizontal locking and retrieving members which are used to hold securely the central locking rod.

The foregoing objectives, features and functions of the present invention can be more readily understood upon a thoughtful deliberation of the following detailed description of preferred embodiments of the present invention in conjunction with the accompanying drawings.

BRIEF DESCRIPTION OF THE DRAWINGS

FIG. 1 shows an exploded view of a first preferred embodiment of the present invention.

FIG. 2 shows an exploded view of a second preferred embodiment of the present invention.

FIG. 3 shows an exploded view of a third preferred embodiment of the present invention.

FIG. 4 shows an exploded view of a fourth preferred embodiment of the present invention.

FIGS. 5-a through 5-d are schematic views illustrating the workings of an instrumentation of the present invention.

DETAILED DESCRIPTION OF THE PREFERRED EMBODIMENTS

Referring to FIG. 1, the first preferred embodiment of the present invention is shown to comprise mainly two horizontal locking and retrieving members 10, a plurality of vertebral locking members 20, and a central locking rod 30.

Each of the two horizontal locking and retrieving members 10 is made up of a locking rod retainer 11 and two locking member retainers 12. The locking rod retainer 11 has a retaining mount 111 and two small threaded holes 112, and two large threaded holes 113. Each of the two locking member retainers 12 consists of a threaded portion 121, a retaining mount 122, and a through hole 123. The threaded portion 121 of the locking member retainer 12 is so dimensioned as to be screwed into the large threaded hole 113 of the locking rod retainer 11. The vertebral locking member 20 comprises a threaded portion 21, a stopping portion 22, and a locking portion 23. The threaded portion 21 is inserted securely into a vertebra (not shown in the drawings) intended to be locked. The locking portion 23 is so dimensioned as to pass through the through hole 123 of the locking member retainer 12. The bendable central locking rod 30 of a cylindrical construction is provided with an elongate slot 32 and a threaded portion 31, with both ends of the central locking rod 30 being retained securely and respectively in the retaining mount 111 of the locking rod retainer 11 by means of two fastening nuts 401 and 402. As a result, the central locking rod 30 is held securely in place by the two horizontal locking and retrieving members 10. The vertebral locking members 20 are fastened securely to the locking member retainers 12 by means of the fastening nuts 411–414. The central locking rod 30 is held securely in place in the retaining mount 111 of the locking rod retainer 11 by means of three small bolts 415, 416 and 417. The small bolt 415 is screwed into the small threaded hole 112 of the locking rod retainer 11 to be stopped in the elongate slot 32 of the central locking rod 30. The locking rod retainer 11 and the two locking member retainers 12 are made separately, as shown in FIG. 1. Each of the two locking member retainers 12 is united with the locking rod retainer 11 by means of the threaded portion 121, which is screwed into the large threaded hole 113 located in the base of the locking rod retainer 11.

The second preferred embodiment of the present invention is shown and illustrated in FIG. 2. Unlike the first preferred embodiment of the present invention, the second preferred embodiment is provided with a locking rod retainer 11' and two locking member retainers 12', which are made integrally. The locking rod retainer 11' has a locking rod retaining mount 111' and a small threaded hole 112'. The locking rod retaining mount 111' is so dimensioned as to receive therein a central locking rod 30' which is further held securely in place by means of a small bolt 41 which is screwed into the small threaded hole 112'. Each of the two locking member retainers 12' is provided thereon with a rough portion 121 and is dimensioned to fit into a through hole 23' of a vertebral locking member 20' which is further provided with a fastening ring 22' and a threaded portion 21'. The vertebral locking member 20' is mounted securely on the locking member retainer 12' by means of a small bolt 42, which is screwed into a small threaded hole (not labeled) located in the fastening ring 22' of the vertebral locking member 20'. Unlike the first preferred embodiment of the present invention, each of the two vertebral locking members 20' is held securely in place on the rough portion 121 of the locking member retainer 12'.

As shown in FIG. 3, the third preferred embodiment of the present invention is basically similar to the second preferred embodiment of the present invention, with the difference being that the third embodiment incorporates a three-point shear clamp mechanism. Accordingly, a locking rod retainer 11" is provided with a locking rod retaining mount 111" and an U-shaped slot 112". A central locking rod 30" is provided with a fastening block 51, which is so dimensioned as to fit into the U-shaped slot 112", and the fastening block 51 so dimensioned as to fit into the locking rod retaining mount 111". The fastening block 51 has a fastening bolt 52, which is threadably secured to and located at one outer side of the locking rod retaining mount 111", that can be fastened within locking rod retaining mount 111" so that the fastening block 51 is shifted along with the central locking rod 30" toward another outer side of the locking rod retaining mount 111" whereby locking rod 30" will engage U-shaped slot 112" on opposite sides of fastening block 51 and fastening bolt 52 will engage locking rod retainer 11" to effect the three-point shear clamp mechanism.

The fourth preferred embodiment of the present invention is illustrated in FIG. 4. It is seen that a locking rod retainer 11''' is provided with a locking rod retaining mount 111''' of a spherical construction. A locking member retainer 12''' is provided with a spherical collar 121'''. Each of two vertebral locking members 20''' is composed of a threaded portion 21''' and a fastening mount 22'''. The fastening mount 22''' has a spherical mount 221, which is so dimensioned as to receive therein the spherical collar 121''' in such a manner that the spherical collar 121''' can be rotated in all directions. Similarly, a central locking rod 30''' is provided with a spherical collar 60 which is so dimensioned as to be rotatably received in the locking rod retaining mount 111''' of the locking rod retainer 11'''. Whenever fastening caps 61, 62 and 63 are rotated on the locking rod retainer 11''' and the two fastening mounts 22''', the spherical collars 60 and 121''' hold firmly and respectively the central locking rod 30''' and the locking member retainer 12''', thereby uniting together the locking rod retainer 11''', the spherical collar 60 and the fastening cap 61. As a result, the spherical collar 60 can not be rotated in the locking rod retaining mount 111''' of the locking rod retainer 11'''; the central locking rod 30''' can not be rotated or moved in the spherical collar. Similarly, the fastening mount 22''' of the vertebral locking member 20''', the locking member retainer 12''' and the spherical collar 121''' can be united together. As shown in FIG. 4, a LUGUE hook 80 may be used as another form of the vertebral locking member.

The present invention may be used in a conventional spinal surgery for stabilizing and retrieving a deformed vertebra, or in a spinal surgery for correcting the scoliosis. As shown in FIGS. 5-a through 5-d, the system according to the embodiment of FIG. 4 of the present invention is shown implanted by a conventional surgical operation in a laterally-crooked spine, without fastening the connecting members 61, 62 and 63 (see FIG. 5c) The central locking rods are rotated in directions indicated by arrows in FIG. 5-b. In the meantime, the relative positions of the horizontal locking and retrieving members are checked and adjusted to correspond to the positions as shown in FIG. 5-d, before the connecting members 61, 62, and 63 are fastened.

The system of the present invention may be made of biocompatible materials, such as the iron-based stainless steel 316 LVM, the Ti-6-4, the cobalt molybdenum chromium alloy, etc.

The locking rod retainer and the locking member retainer of the horizontal locking and retrieving member of the present invention may be made integrally or made separately and then coupled threadably.

Any suitable spinal pin or LUGUE III spinal system may be used as a vertebral locking member of the present invention.

The central locking rod of the present invention may be of any shape, depending on the surgical requirement. If the system of the present invention is used for a scoliotic correction, the central locking rod may be of a curved cylindrical construction, or a curved flat cylindrical construction, or a curved oval cylindrical construction, or a curved rectangular columnar construction, etc. The curvature of the central locking rod of the present invention is dependent on the curvature of the vertebra under treatment or on the lateral curvature of the spine receiving the treatment. In case the system of the present invention is used in a surgical operation for locking and retrieving a deformed vertebra, the central locking rod of the present invention may be of a cylindrical construction, or a flat cylindrical construction, or an oval cylindrical construction, or a rectangular columnar construction, etc. If necessary, such a central locking rod may be curved to an extent that the curved central locking rod can cooperate well with the deformed vertebra receiving the treatment.

According to the present invention, the fastening of the locking rod to the locking rod retainer can be best achieved by means of a nut-bolt fastening system, or a side screw fastening system, or an upper nut-bolt fastening system or a TSRH three-point shear clamp device made by Danek Corporation of the United States, or an ISOLA V-grooved connection system, or a convention spherical fastening system. Similarly, the fastening of the vertebral locking member to the locking member retainer can be accomplished by means of the fastening systems described above. It must be noted here that any one of the fastening systems described above may be made separately as an independent member or made integrally as a part of the horizontal locking and retrieving member or the vertebral locking member.

In case the situation calls for the use of an additional fastening means, an auxiliary fastening, such as an auxiliary device for fastening the locking rod or a wire-rope auxiliary fastening device, may be used to enhance the fastening.

The embodiments of the present invention described above are to be regarded in all respects as merely illustrative and not restrictive. Accordingly, the present invention may be embodied in some other forms without deviating from the spirit thereof and is therefore to be limited only by the scope of the following appended claims.

What is claimed is:

1. A vertebral locking and retrieving system comprising:
    a plurality of horizontal locking and retrieving member sets, with each of said sets comprising a locking rod retainer having two opposing sides and two locking member retainers, each of said locking member retainers including a first portion fastened to a respective one of said opposing sides of said locking rod retainer and a second portion defining a retaining mount;
    a plurality of vertebral locking members, each of said vertebral locking members having a first end adapted to be secured within a respective vertebra and a second end fastened to a respective one of said retaining mounts;
    a central locking rod adapted to extend between and to be mounted to said locking rod retainers; and
    connecting means for fastening the second ends of said vertebral locking members to respective retaining mounts of said locking member retainers and for fastening said central locking rod to said locking rod retainers of said horizontal locking and retrieving member sets;
    wherein a horizontal locking of a vertebra is achieved by said horizontal locking and retrieving member sets while a longitudinal locking of said vertebra is attained by said central locking rod connecting said horizontal locking and retrieving member sets.

2. The vertebral locking and retrieving system of claim 1, wherein the first end of each of said vertebral locking members comprises a threaded portion, each threaded portion being adapted to be threadably secured with a respective vertebra.

3. The vertebral locking and retrieving system of claim 1, wherein each of said locking rod retainers includes a retaining mount in the form of a slot adapted to receive said central locking rod.

4. The vertebral locking and retrieving system of claim 3, wherein said central locking rod is formed with an elongated slot and said connecting means for fastening said central locking rod to said locking rod retainers includes a plurality of connecting members, each of said connecting members being attached to a respective one of said locking rod retainers and extending into said elongated slot.

5. The vertebral locking and retrieving system of claim 3, wherein the slot of said retaining mount for said central locking rod is generally U-shaped.

6. The vertebral locking and retrieving system of claim 5, further including a fastening block carried by said central locking rod, said fastening block being adapted to be received and secured within said U-shaped slot of said retaining mount for said central locking rod.

7. The vertebral locking and retrieving system of claim 3, further including a spherical collar carried by said central locking rod, said spherical collar being adapted to be pivotally mounted within a respective one of said retaining mounts of said central locking rod.

8. The vertebral locking and retrieving system of claim 1, wherein the first portion of each of said locking member retainers is threadably secured within a respective one of said opposing sides.

9. The vertebral locking and retrieving system of claim 1, wherein each of said locking rod retainers defines a roughened portion to which the second end of a respective one of said vertebral locking members is attached.

10. The vertebral locking and retrieving system of claim 1, wherein each of said locking rod retainers includes a hole extending therethrough which defines a retaining mount for said central locking rod.

11. The vertebral locking and retrieving system of claim 1, wherein the retaining mount defined at the second portion of each of said locking member retainers comprises a spherical collar which is pivotally attached to the second end of a respective one of said vertebral locking members.

* * * * *